United States Patent
Shile

(10) Patent No.: US 6,669,482 B1
(45) Date of Patent: Dec. 30, 2003

(54) METHOD FOR TEACHING INTERPRETATIVE SKILLS IN RADIOLOGY WITH STANDARDIZED TERMINOLOGY

(76) Inventor: Peter E. Shile, 7317 Teasdale Ave., St. Louis, MO (US) 63130

( * ) Notice: Subject to any disclaimer, the term of this patent is extended or adjusted under 35 U.S.C. 154(b) by 341 days.

(21) Appl. No.: 09/613,336

(22) Filed: Jun. 30, 2000

Related U.S. Application Data

(60) Provisional application No. 60/141,726, filed on Jun. 30, 1999.

(51) Int. Cl.[7] .............................................. G09B 23/28
(52) U.S. Cl. ....................................................... 434/262
(58) Field of Search .................................. 434/262, 267

(56) References Cited

PUBLICATIONS

B–Rads Thirds Edition, American College of Radiology, Breast Imaging Reporting and Data System, Apr. 1998.*
Metz CE. "ROC methodology in radiologic imaging". Invenstigative Radiology. 1986; 21: 720–733.*
Kerlikowske et al. "Variability and accuracy in mammographic interpretation using the American College of Radiology Breast Imaging Reporting and Data System". Journal of the National Cancer Institute; Bethesda; Dec. 2, 1998 vol. 90 issue 23 pp. 1801–1809.*
Breast Cancer Screening/Prevention. Imaginis. Retrieved from the Internet [Mar. 20, 2002]URL:<http://www.pinnacleimaging.com.bresthealth/mqsa.asp?mode=1>.*
Carl J. D'Orsi, M.D. & Daniel B. Kopans, M.D. "Mammography Interpretation: THe BI–RADS Method" American Family Physician. vol. 55, No. 5, Apr. 1997.*
"The BI–RADS Lexicon" Retrieved from the Internet [Mar. 20, 2002]. URL:<http://www.eesoftware.net/advscripts/BI-RADS.htm>.*
Federal Register, Part II, Department of Health and Human Services, Food and Drug Admin. 21 CFR Parts 16 and 900, Quality Mammography Standards; Final Rule, Oct. 28, 1997.
Edward A. Sickles, MD; Steven H. Ominsky, MD; Richard A. Sollitto, MD; Helen B. Gavin, MD; Debra L. Monticciolo, MD; Medical Audit of a Rapid–Throughput Mammography Screening Practice: Methodology and Results of 27,114 Examinations; May 1990; Radiology.

(List continued on next page.)

*Primary Examiner*—Michael O'Neill
*Assistant Examiner*—Julie Brocketti
(74) *Attorney, Agent, or Firm*—Polster, Lieder, Woodruff & Lucchesi, L.C.

(57) ABSTRACT

A training method for improving diagnostic accuracy and reducing variability in the interpretation of radiologic exams. Exam images, whether presented on radiographic film, on photographic paper, or on a computer monitor, are interpreted using standardized feature descriptors, such as in BI-RADS. The exam interpreter uses the feature descriptors to characterize findings in exam images and provides an assessment and conclusion concerning the presence of biologic processes that would have caused the image finding. Evidence for the presence or absence of these biologic processes is obtained. Measures of diagnostic accuracy are calculated from these data and all this information is tracked and associated with the exams. Subsequent to image interpretation, exam findings and tracked data are reviewed in a case-based manner to teach the image interpreter to better understand the relationship between features and the biologic processes that they are associated with, thereby improving the interpreter's diagnostic accuracy and reducing variability in their characterization of image findings. Repetitive use of this method further improves diagnostic accuracy and reduces variability in the characterization of image findings.

27 Claims, 3 Drawing Sheets

OTHER PUBLICATIONS

Baker, et al.; Breast Imaging Reporting and Data System Standardized Mammography Lexicon: Observer Variability in Lesion Description; Apr. 1996.

Michael N. Linver, MD; Stuart B. Paster, MD; Robert D. Rosenberg, MD; Charles R. Key, MD; Christine A Stidley, PhD; Warren V. King; Radiology; Jul. 1992.

RSNA; 1997 Scientific Program; Radiological Society of North America; Nov. 1997 vol. 205(P); Supplement to Radiology.

Science to Practice; RSNA 1998; Nov. 1998 vol. 209(P); Supplement to Radiology, 1998 Scientific Program, Radiological Society of North America.

Liberman et al.; The Breast Imaging Reporting and Data System: Positive Predictive Value of Mammographic Features and Final Assessment Categories; Jul. 1998.

Bi-Rads Second Edition, Breast Imaging Reporting and Data System, American College of Radiology, Sep. 1995.

Bi-Rads Third Edition, American College of Radiology, Breast Imaging Reporting and Data System, Apr., 1998.

* cited by examiner

METHOD FOR TEACHING INTERPRETATIVE SKILLS IN RADIOLOGY WITH STANDARDIZED TERMINOLOGY

CROSS-REFERENCE TO RELATED APPLICATIONS

U.S. Provisional Patent Application 60/141,726, filed Jun. 30, 1999.

STATEMENT REGARDING FEDERALLY SPONSORED RESEARCH OR DEVELOPMENT

Not applicable.

BACKGROUND OF THE INVENTION

The invention relates to a method for improving a radiologists or other interpreters skills in interpreting radiologic images whether film images viewed on a multiviewer or the like, or digital images viewed on a computer screen. The method includes use of standardized terminology during interpretation of radiologic studies to characterize image findings. The method tracks an interpreter's use of this terminology in addition to their assessments and conclusions concerning the presence or absence of biological processes that cause the image finds and tracks evidence for the presence or absence of these biological processes. The method further employs repetitive feedback to interpreters concerning their diagnostic accuracy and use of standardized feature descriptors to refine their understanding of the appropriate use of the terminology.

Variability of Interpretations in Radiology

Variability in the interpretation of radiological exams is a known phenomenon, and has recently received considerable attention in the area of breast imaging. For example, recent research has demonstrated marked variability in radiologists' interpretation of mammograms (Elmore, 1995 & 1998; Beam, 1996). The authors of these studies have noted the need for efforts to improve accuracy and reduce variability in the interpretation of mammograms. Unlike analytic tests (e.g. serum electrolytes), the interpretation of radiologic tests involves a significant amount of subjective judgment. This phenomenon has been discussed in numerous publications (Elmore, 1995; Beam, 1996), and includes both (a) failures in detection (i.e., failure to identify an abnormality), and (b) failures of characterization (e.g., failure to properly classify an abnormality as benign or malignant once its features have been assessed). The method of the present invention addresses this second source of variability, focusing on a method for improving diagnostic accuracy and reducing the variability of an interpreters' characterization of abnormalities seen on radiologic examinations.

Standardized Reporting for Radiologic Examinations

Breast imaging is one of the first subspecialties of radiology to embrace standardized reporting. Standardized reporting uses defined terminology and report formats to improve consistency and reduce confusion in the reporting of image findings and abnormalities. Mammography is the first area of breast imaging in which widespread use of standardized reporting is becoming common practice. This results, in part, from Federal regulations which went into effect Apr. 28, 1999, requiring all mammographic facilities in the United States to use standardized assessment and recommendation terminology at the end of mammographic reports. The assessment and recommendation language is nearly identical to that used in the American College of Radiology's (ACR's) Breast Imaging and Reporting Data System (BI-RADS). BI-RADS was developed for standardized mammography reporting and was first released in 1993 (Kopans, 1993). The ACR's promotion of BI-RADS helped influence the Food and Drug Administration's (FDA's) requirement that standardized assessment and recommendation terminology appear at the end of mammographic reports. The promotion of BI-RADS has also prompted development of standardized terminology for other imaging modalities. For example, standardized reporting terminology for breast ultrasound is being pursued by several groups (ACR Bulletin 1999; Hawkins, 1998).

Image Feature Assessment Using Standardized Terminology

Standardized reporting formats include lexicons of feature descriptors used to categorize image findings and abnormalities (Kopans, 1993; D'Orsi, 1995 & 1998; Hawkins, 1998). In the case of BI-RADS, D'Orsi, et al (1993) have attempted to group BI-RADS lexicon features according to the probability of their association with malignancy. However, it is only recently that the association of BI-RADS features with benign and malignant breast disease has been empirically evaluated (Lieberman, 1998). New and/or altered descriptors that better discriminate between benign and malignant breast disease will be incorporated into BI-RADS as they are discovered. As these type of improvements are made in BI-RADS, proper use of the feature descriptors will help guide radiologists to more accurate characterization of mammographic findings. The same is anticipated for feature descriptors of other standardized reporting systems.

Feature-base Training for Reducing Variability in Feature Assessment

Use of standardized feature descriptors in the interpretation of radiologic studies is subject to variability (Baker, 1996; Shile, 1997; Berg, 1997; Orel, 1997). Training radiologists to appreciate the range of presentations of standardized features can reduce observer variability in the use of these descriptor terms. However, it is important to now provide a method for training radiologists to understand the relationship between standardized feature descriptors and pathological entities seen on radiological exams. The current invention is directed to such a method.

Practice Audits for Improving Diagnostic Accuracy in Radiologic Interpretation Practice audits in breast imaging have been used for a number of years to improve the skills of interpreters. Hence the Agency for Health Care Policy and Research (AHCPR) has strongly encouraged them (Basset, 1994), and the AHCPR audit recommendations became Federal Law in 1999 (Federal Register, 1998). Breast imaging facilities are now required to track mammography assessments and recommendations according to structured assessment and recommendation categories. This aides practice in calculating profiles such as true positive, true negative, false positive and false negative rates, as well as sensitivity, specificity and positive predictive values. Audits containing this information have been shown to be a powerful educational tool for refining radiologist's interpretive skills (Bird, 1992; Sickles, 1990; Spring, 1991; Linver 1992). However, this type of audit information only provides radiologists with a general overview of the strengths and weaknesses of their interpretive skills. For example, these audits enable radiologists to identify poor specificity in mammographic interpretations. They do not provide radiologists with mechanisms to examine the relationship between features of image findings and diagnostic decision making. The method of the current invention provides this type of mechanism, and like a practice audit, is a powerful educational tool.

BRIEF SUMMARY OF THE INVENTION

The primary object of the present invention is a training method to improve the accuracy and reduce the variability of anyone who reads and interprets radiologic examinations. The method tracks the reader's (image interpreter's) diagnostic accuracy and use of standardized feature descriptors during interpretation of radiologic examinations. The method is not only useful for training readers how to appropriately use descriptors of a standardized reporting system, but it also leads to a detailed understanding of the association of findings with specific types of pathology (e.g., benign and malignant disease). As described herein, the method utilizes repetitive feedback concerning an interpreter's diagnostic accuracy and use of standardized terminology during exam interpretation. It improves accuracy of interpretations and reduces variability in the use of standardized terminology.

It is a further object of the invention to document a radiologist's diagnostic accuracy and use of standardized feature descriptors for review and training. To achieve this, the radiologist is asked to describe image findings using standardized terminology during exam interpretation. For each image finding, the radiologist is also asked to provide their assessment concerning the presence of a biological process that has caused the finding. These assessments are used to calculate the radiologist's diagnostic accuracy, this being done, for example, using Receiver Operator Characteristic (ROC) analysis (Metz, 1986) in which ROC curves are plotted and curve areas are calculated. Other accuracy and performance measures include, for example, positive and negative predictive values, sensitivity and specificity values, likelihood ratios, true negative and false negative values, and true positive and false positive values.

An additional objective of the invention is to track outcome data that establishes the presence or absence of biological processes. These data are used in the calculation of the interpreter's diagnostic accuracy. In the case of a mass seen on a screening mammogram, for example, the outcome assessment of interest is a determination of whether the finding is the result of benign or malignant process. There are several ways of determining this. A biopsy of the mass, with histologic analysis, would determine not only whether the mass is benign or malignant, but would also provide the specific histology of the process causing the radiologic finding. Alternatively, if the mass was not biopsied and considered benign, clinical and radiologic follow-up could establish benignancy. For example, if the mass remains unchanged on subsequent mammograms and there is no clinical evidence of change or malignancy, this would be suitable confirmation of a benign lesion. While these examples involve patient outcomes in screening mammography, standards for confirming biological processes in other types of radiological examinations are known in the art.

A further objective of the invention is to track patient demographic data that is important to the interpretation of a radiologic examination. In the interpretation of mammograms, for example, it is important to track patient age since age influences the probability of a person having breast cancer.

Another objective of the invention is to provide feedback to trainees concerning their diagnostic accuracy and their use of standardized feature descriptors. During feedback, tracked data are reviewed with associated exam images. Feedback sessions enable trainees to review the features of image findings, their descriptions of the features, and the biologic processes that caused the findings. Calculated values of diagnostic accuracy are presented to trainees and provide them with an assessment of their performance. With knowledge of their diagnostic accuracy and the biologic process that caused each image finding, trainees review findings and focus on more accurately describing findings and predicting the biologic processes imaged in radiologic exams.

The method enables several types of feedback to the trainee, and these differ by the manner in which the collected data are sorted for review. One of these involves sorting the data by individual feature descriptors. This type of sorting enables the trainee to review features and their description of them for the purpose of identifying inconsistencies in their use of descriptors.

The method also enables data to be sorted according to the trainees assessments for the presence of different biologic processes and helps the trainee to better appreciate which features are good and bad predictors of a biologic process (e.g. malignancy). When data are sorted for review in this manner, feedback sessions enable the trainee to examine cases in which they were highly confident about the presence of a biologic process and look at the image features that contributed to this certainty. This enables trainees to more accurately predict a disease process.

Similarly, when data are sorted by patient outcome, feedback focuses on the types of features and the range of features that characterize particular types of histology. This aids the test taker in understanding which features predict particular types of histology better than others. By seeing features that are present in multiple types of histologic processes, trainees are also able to better appreciate subtle differences in features that will help them to achieve greater accuracy in their interpretations.

Another object of the invention is to provide feedback to trainees concerning the distribution of pathology and associated image findings in different patient populations. For example, the types of breast pathology and image findings present in a population of women undergoing screening mammography is different than in a population of women undergoing image-guide breast biopsy. To enable the trainee to learn the range of image findings in different patient populations, the method employs standard sampling techniques, well-known in the art, to create image review sets with appropriate composites of findings and/or pathology for defined patient populations.

A further object of the invention is repetitive feedback. After intervals that enable the accumulation of sufficient data for additional feedback sessions, newly interpreted exams are reviewed with tracked data to provide reinforcement concerning the appropriate use of standardized feature descriptors.

In accordance with the invention, generally stated, a training method is described by which a radiologist's or other exam interpreter's ability to interpret radiologic studies of a patient, whether presented on film, or in a digital format is measured. Initially, the radiologist or image interpreter views and interprets a set of radiologic exams. For each viewed image in an examination, a finding is made and the radiologist or image interpreter describes the features of the finding using BI-RADS descriptors. An assessment of the presence of a malignancy is also provided. The results are then reviewed to assess both the accuracy of the diagnosis and the use of the descriptors. After this initial image interpretation, the radiologist or image interpreter reviews their diagnostic accuracy and use of feature descriptors, in addition to patient outcomes. Subsequent image interpretation and case review aids the radiologist or image interpreter in improving his or her proficiency in diagnosis and use of feature descriptors. Other objects and features will be in part apparent and in part pointed out hereinafter.

DETAILED DESCRIPTION OF THE INVENTION

While the method of the invention is for training in the interpretation of mammograms using the standardized feature descriptors contained in BI-RADS, the method is applicable to any radiologic imaging modality which is interpreted using a standardized reporting system. The fundamental objective of the method is both to reduce variability in the use of descriptors and to improve diagnostic accuracy in mammographic interpretation.

Image Datasets

A number of image datasets can be used for mammography training. Examples of images used therein are shown in FIGS. 1–6. Conventionally, radiologic images were captured on film, and the images were placed on a light box or multiviewer for reading by the radiologist. More recently, the images are acquired in digital format, stored in a computer memory, and can also be viewed on photographic paper or a computer monitor.

The method requires that trainees interpret a set of mammograms so that data can be collected. For a practicing radiologist or other interpreter, these can be mammograms interpreted in the course of their practice, provided that the data discussed below are collected (see Image Interpretation). Alternatively, mammographic test sets can be created to be read by an interpreter. In some instances, it can be of value to have findings on exams in test sets clearly identified. This can be done by circling the findings on the mammographic film, for example, but other means can also be used.

Figure 1:
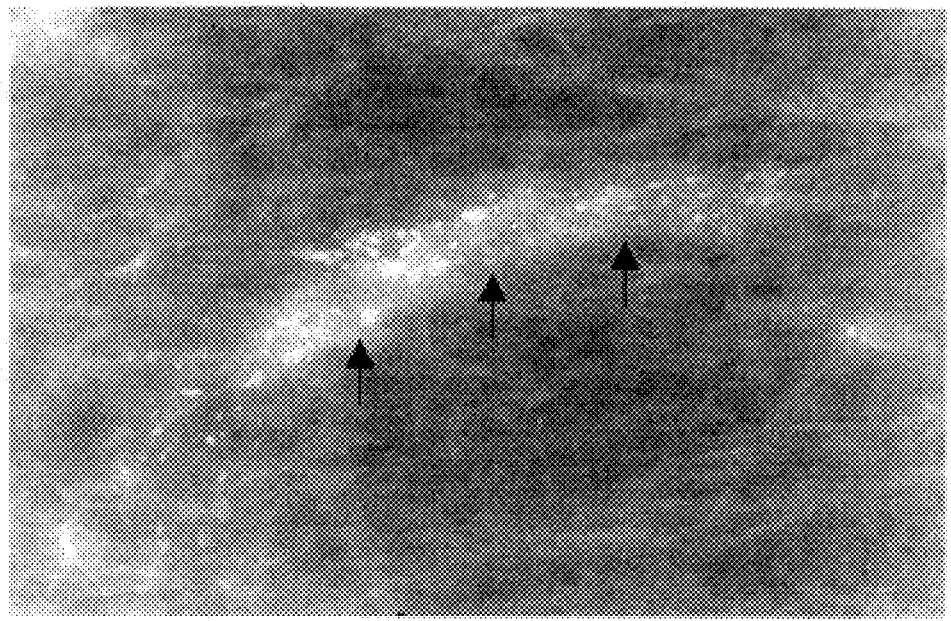
FIG. 1 is representative example of a radiologic image comprising a portion of a mammographic examination viewed by a radiologist or other image interpreter.

FIG. 1 is from a mammogram and depicts calcifications in a patient's right breast (arrows) which were imaged in the craniocaudal projection.

Figure 2:
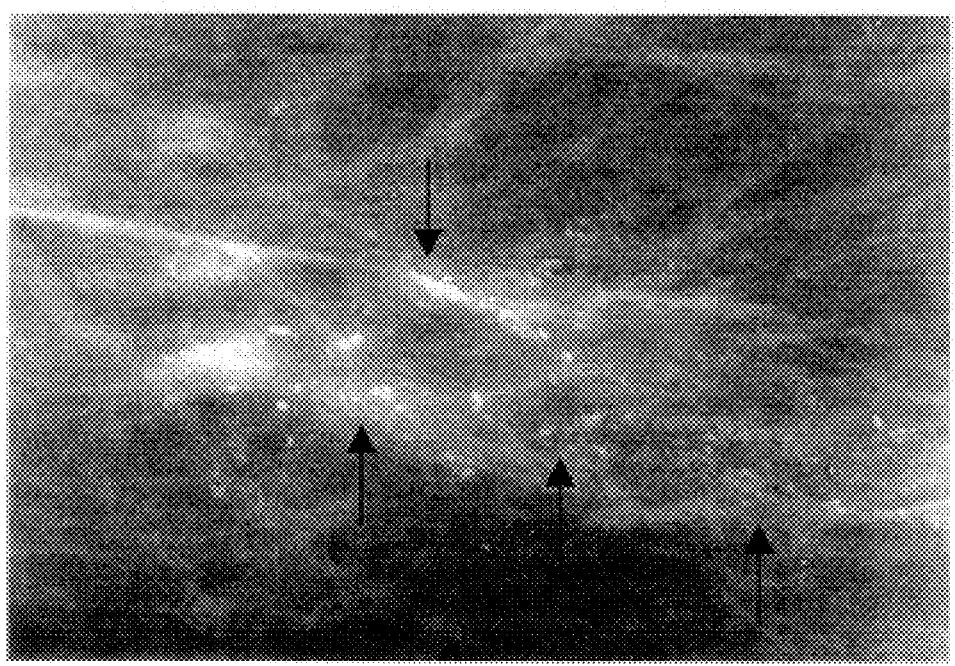
FIG. 2 is representative example of a radiologic image comprising a portion of a mammographic examination viewed by a radiologist or other image interpreter.

FIG. 2 depicts the same calcifications as in FIG. 1 (arrows), but imaged in the mediolateral projection. Using the BI-RADS descriptors for calcification type, an appropriate characterization of these calcifications would be pleomorphic/heterogeneous calcifications. The biologic process that caused these calcifications was early breast cancer, known as ductal carcinoma in-situ (DCIS), and was confirmed by biopsy. Calcifications with these features are commonly associated with breast cancer.

Figure 3:
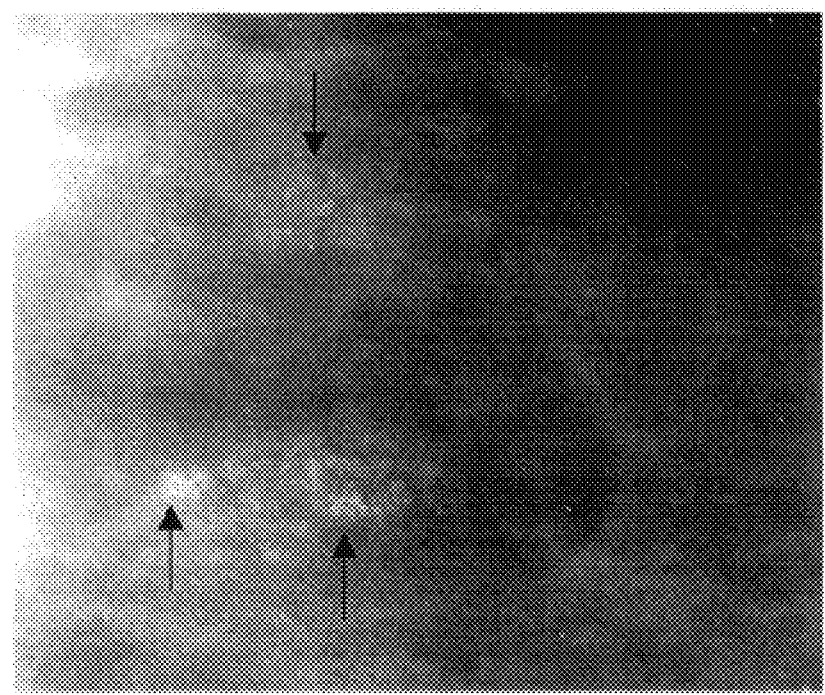
FIG. 3 is representative example of a radiologic image comprising a portion of a mammographic examination viewed by a radiologist or other image interpreter.

FIG. 3 is from a mammogram and depicts calcifications in a patient's left breast (arrows) which were imaged in the craniocaudal projection.

Figure 4:
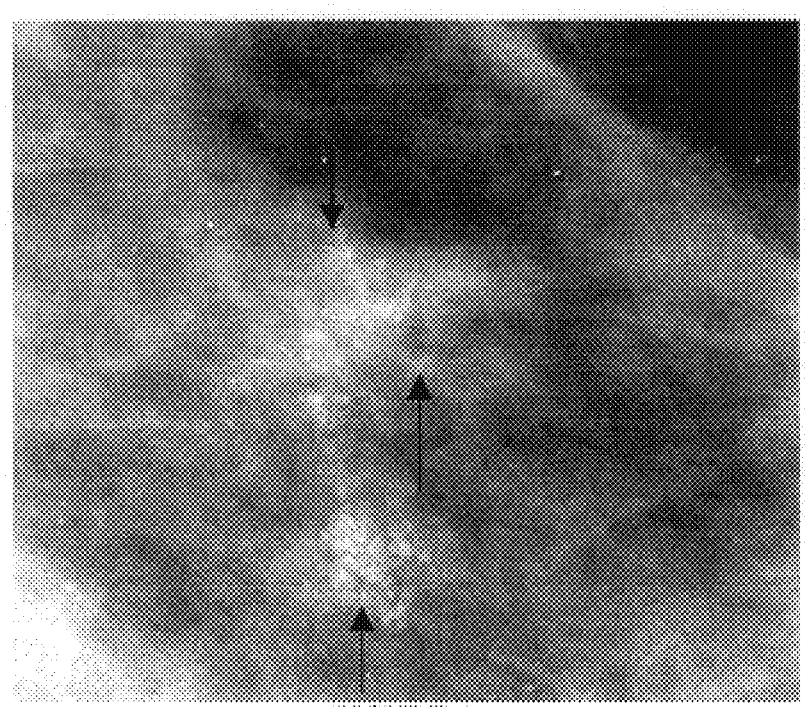
FIG. 4 is representative example of a radiologic image comprising a portion of a mammographic examination viewed by a radiologist or other image interpreter.

FIG. 4 depicts the same calcifications as in FIG. 3 (arrows), but imaged in the mediolateral projection. Using the BI-RADS descriptors for calcification type, an appropriate characterization of these calcifications would be amorphous/indistinct calcifications. The biologic process that caused these calcifications was the same type of early breast cancer that was depicted in FIGS. 1 and 2. Amorphous/indistinct calcifications have a range of appearances and are less frequently associated with breast cancer than are pleomorphic/heterogeneous calcifications. The method of this invention enables interpreters to learn the range of appearances of amorphous/heterogeneous calcifications and to learn subtle features which help to distinguish between those involved in benign processes and those involved in malignant processes.

Figure 5:
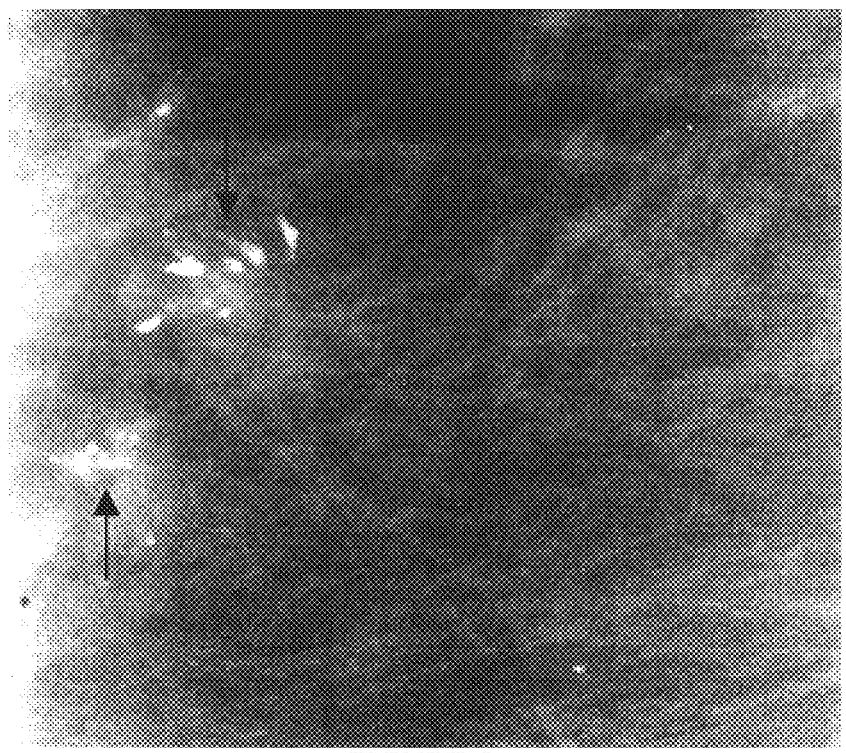
FIG. 5 is representative example of a radiologic image comprising a portion of a mammographic examination viewed by a radiologist or other image interpreter.

FIG. 5 is from a mammogram and depicts calcifications in a patient's left breast (arrows) which were imaged in the craniocaudal projection.

Figure 6:
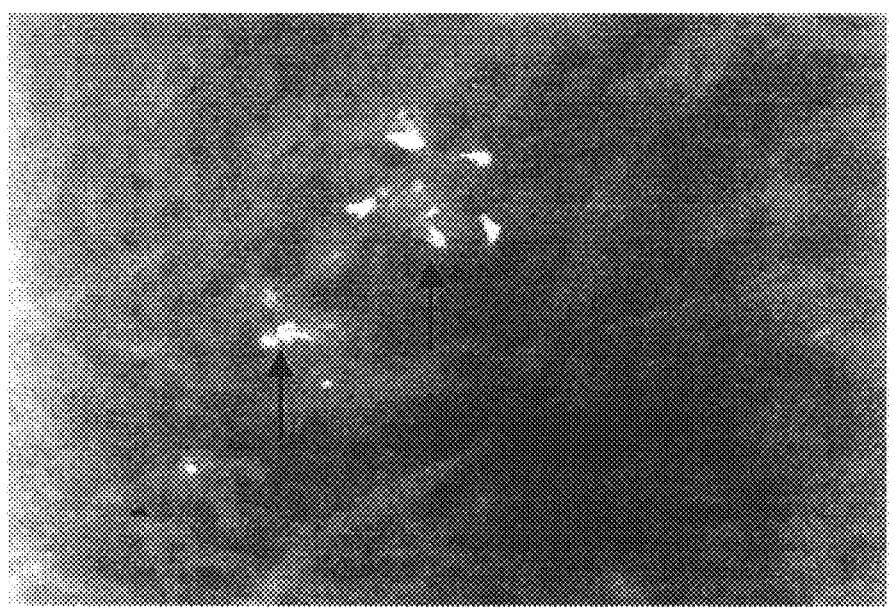
FIG. 6 is representative example of a radiologic image comprising a portion of a mammographic examination viewed by a radiologist or other image interpreter.

FIG. 6 depicts the same calcifications as in FIG. 5 (arrows), but imaged in the mediolateral projection. Using the BI-RADS descriptors for calcification type, appropriate characterization of these calcifications might be either pleomorphic/heterogeneous calcifications or dystrophic calcifications. The biologic process that caused these calcifications was a nonmalignant scarring process, confirmed by biopsy. While somewhat similar in appearance to the calcifications in FIGS. 1 and 2, the method of this invention would help to train an interpreter to better appreciate and characterize subtle differences between calcifications in DCIS and scarring. This leads to improved diagnostic accuracy and reduced variability in the interpretation of mammograms.

With respect to the datasets, a first set is representative of the screening environment and is collected from consecutive cases read in a screening practice or group of practices, or by sampling cases from a screening program or group of programs. The sampling produces exams representative of those obtained from a screening referred population. However, since many women undergoing screening mammography have no breast pathology, this dataset should include only those exams that demonstrate findings. These can be either benign or malignant findings. In a screening population, the majority of findings are benign. In order to perform a meaningful ROC analysis, the dataset preferably should include at least 50 screening exams. However, to determine the exact number of cases in the screening dataset, it is important to realize that satisfactory ROC analysis is dependent on the assessments of malignancy assigned by individual readers and the number of malignancies in the test set. Thus test set size is not necessarily known in advance and assurance of adequate size for ROC analysis may require pilot testing or employing another method to assess adequate test set size. For the purposes of comparing changes in diagnostic accuracy in subsequent testing, it will also be understood that confident determination of differences in performance could necessitate a greater number of exams in the test set.

A second test set consists of cases referred from screening mammography for diagnostic evaluation. The representation and distribution of findings in this test set differs from the screening test set and typically contains a larger percentage of malignancies (cancers). Exams for this test set should be collected from consecutive cases referred for diagnostic work-up from a screening mammography practice or group of practices. They can also be collected by sampling cases from a mammography practice or group of practices. Sampling may be performed so the test set contains exams representative of a population of patients referred from screening mammography for diagnostic evaluation. Only cases with confirmed findings are included in this data set. Sometimes cases referred for diagnostic evaluation do not have any findings confirmed at the time of diagnostic work-up. This can be because the findings on screening exams are not real, but result from the superimposition of normal breast tissue. These types of cases are well known to those skilled in the art and are not included in the test set. Factors that influence adequate size of this test set are the same as for the screening dataset. However, the number of malignancies in patients referred from screening for diagnostic evaluation is higher. Thus, this dataset may be smaller than the screening mammography dataset.

A third image test set consists of mammograms from patients referred for biopsy. These can be collected from consecutive cases referred for biopsy from a single practice or group of practices. Alternatively, they can be collected from a sampling of cases from a single practice or group of mammography practices so that the included exams are representative of a population of patients referred for breast biopsy. An important subset of this test set are patients referred for biopsy who have mammographic abnormalities with no corresponding palpable abnormality. This subset of patients form a separate test set or are included as a subgroup in all of the biopsy referred cases. Again, test set size is influenced by the factors discussed above. However, the proportion of malignancies in this test set are likely higher than in the ones discussed above. Accordingly, this test set is typically smaller than the others. During interpretation sessions with a test set, iy may be useful to have findings on exams in the test set clearly identified. This can be done by circling findings on the mammographic film, for example, but other means can also be used.

Proof of Etiology for Mammographic Findings

Each finding in an interpreted exam requires "proof" of etiology. "Proof" in the context of this invention is defined as either histologic proof of the image finding (obtained as a result of biopsy), or imaging and clinical evidence of benign disease. When tissue histology is used as "proof", it is desirable to obtain these results from the written pathology report of the biopsy specimen. At times, however, pathology reports are not available, but follow-up with patients' referring doctors or with the patients themselves can establish the results of biopsy. In addition to biopsy, benign disease can also be established by mammographic and clinical follow-up of the patient. Stable findings over a period of two years is considered adequate "proof" of benignancy. Other types of clinical "proof" are also suitable and well know in the art. For example, clinical and imaging proof of a benign mass on a mammogram could include needle aspiration that demonstrates a cyst with resolution of the mass on subsequent mammography.

Patient Demographics

As discussed previously in the Summary section, patient demographic data may be necessary for exam interpretation. These data include, but are not limited to patient age, breast cancer risk factors, breast surgical history, and history of exogenous hormone use.

Data Storage

In the preferred embodiment of this invention, data from interpreted images or exams; including, for example, proof of etiology of image findings and demographic data on patients from whom the images were obtained, are stored and tracked in a computer database. However, paper records or other forms of storage and tracking can also be used. Responses from readers during image interpretation (discussed below) are stored in the same database. This facilitates data manipulation and sorting prior to exam feedback sessions.

Image Interpretation

Image interpretation is performed in a mammography reading room, or an environment that closely simulates one. This can be a dark, quiet room with a mammography viewbox or mammography film multiviewer, or a computer monitor or screen on which the images are displayed. Interpreters can use instruments normally available to them during interpretation of mammograms. Where film is used, these include; for example, a magnifying lens, a bright light for viewing overexposed areas of film, and a ruler. For digital images, a graphic user interface, allows the test subject to navigate through the images. Where the images are available in various degrees of resolution, the subject can move from level of resolution to another as appropriate.

For interpretation of test sets, it is preferable to randomly arrange the order of the exams for each image interpreter. This minimizes order effects if one interpreter's results are to be compared to another's or if one interpreter reads a test set several times, and results from those readings are to be compared. Issues and methods with regard to minimizing order effects are well-known in the art of test design and are not described.

Image interpreters interpret each exam by using BI-RADS feature descriptors to describe each of the findings identified in an exam. For each such finding the interpreter provides an assessment concerning the presence of malignancy. For example, a 10 point scale might be used, where 10 indicates virtually certain malignancy and 0 indicates virtually certain benign disease (no malignancy). However, scales other than this can be used. Response values during interpretation are recorded in any number of ways, including on paper or as computer input. All of the exam images are interpreted in the same manner, and testing is complete when all the images have been interpreted.

Image interpretation need not be completed in one continuous sitting, nor in a single day. In general, image interpreters takers are given as much time as they require to interpret exams. However, in some test situations only a limited amount of time is allowed for interpretation of the test set. For example, test taking may be time limited so the test taker understands the influence of time on their interpretive skills.

Performance Measurement of Image Interpreters

After interpretation is completed, performance values are calculated. ROC analysis is the primary performance value for establishing an interpreter's diagnostic accuracy. However, other performance measures are equally useful and should be calculated for feedback to the interpreter. These include, but are not limited to: (a) the positive and negative predictive values of individual and groups of descriptors for both malignancy and for specific types of histology; (b) likelihood ratios for different types of disease and histology in the presence of specific feature descriptors; and (c) true negative, false negative, true positive, and false positive results for test interpretation. Methods for calculating these performance values are well known to those skilled in the art and again are not described.

Data and Exam Sorting

Performance data along with exam images, patient data, and response data are sorted and grouped for feedback to the image interpreter. Data sorting is as previously described and includes sorting and grouping data and cases by individual feature descriptors or groups of descriptors. Thus when these data and test set images are presented back to the reader, all findings described with the same descriptor are presented to the reader as a single group of cases. In review sessions, this permits the image interpreter to review all the cases in which they use the same descriptor. This enables them to examine the range of the appearance of this described finding in the test set.

Data is also sorted by confidence value for malignancy, or by histological type. The rationale for presenting the interpreter with images and data sorted in these ways were discussed earlier. When data are sorted by finding etiology, feedback to the image interpreter is similar, but now the focus is on the range of features used to describe a particular type of histology. This aids the interpreter in understanding which features are the best predictors of particular types of histology. Review of data sorted by confidence value for malignancy enables the interpreter to examine the range of values assigned to lesions characterized with different descriptors and to identify high and low probability descriptors of different diseases.

Feedback to the Image Interpreter

Feedback to the image interpreter is case-based. Preferably, feedback sessions take place in the same or similar environment as for image interpretation. Images from the image dataset are grouped and presented according to the method chosen for data sorting. For example, if data was sorted by feature descriptor (e.g., mass margins) then exams with findings described by the descriptor subtype (e.g., lobulated margins) are presented together. Exams with findings described by another subtype descriptor (e.g., spiculated margins) are presented as a separate group. Exam images are then reviewed with proof of finding etiology, patient demographic data, and response and performance data. Feedback sessions enable image interpreters to review their use of feature descriptors and to better understand the relationships between individual or groups of descriptors and known biological processes imaged in the mammographic examinations. Knowledge of their diagnostic accuracy, confidence values for malignancy assigned to the findings, proof of finding etiologies, and patient demographics are reviewed with the image interpreter's use of descriptors to gain an improved understanding of use of these feature descriptors to more accurately predict the biological processes are captured in the images.

In general, for feedback sessions where data and exams are sorted by BI-RADS feature descriptors, only one type of BI-RADS descriptor category is reviewed in a given feedback session. For example, if data are sorted by calcification morphology, cases are grouped for review by the subtypes of calcification morphology (e.g., amorphous, heterogeneous, fine branching, etc.). This precludes review of images based on a sorting of the data by calcification distribution. Review of the data related to calcification distribution requires a separate feedback session. To review data related to all BI-RADS feature descriptors, a number of feedback sessions are required to completely review any test set. For example, separate feedback sessions are required for each of the following categories of BI-RADS features description: mass shape, mass margins, mass density, calcification type, and calcification distribution.

When data are sorted by confidence values for malignancy, only a single feedback session may be necessary. For example, it frequently occurs that only one finding is noted for evaluation in a patient exam. When responses and images are sorted by assigned confidence values, images are presented in ascending or descending order of the confidence values assigned to the finding in each of the exams. The reviewer reviews the images, proof of finding etiology, patient demographic data, and response and performance data, and examine feature descriptors that have a high and low probability of predicting malignant and benign disease. Similarly, when data are sorted by pathologic/histologic entity, only a single feedback session may be necessary. Again, this is especially true when only one finding is identified for evaluation in a patient exam. For this image, there is only one type of known pathology/histologic process per exam. Hence responses and images are presented in groups that contain an individual disease processes. Image interpreters review the images, proof of finding etiology, patient demographic data, and response and performance data and examine the feature descriptors that best identify each disease process.

Repetitive Feedback

Regardless of the manner in which data are sorted, the purpose of the feedback sessions is to refine exam interpreter's use of a descriptor so they are able to accurately differentiate between benign and malignant breast disease and to more accurately identify specific pathological process. Once an individual's use of descriptors is defined and reviewed, additional rounds of exam interpretation and review are used to further refine understanding and use of the descriptors. Follow-up evaluation with the same or similar image data sets enables the examinee to determine whether their subsequent understanding and use of standardized feature descriptors is more consistent and whether their diagnostic accuracy is improving. For example, subsequent evaluation might be used to establish whether the positive or negative predictive value of ones use of a feature descriptor is improving.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

References

*ACR Bulletin* 1999, 55(6): 14–19. Working Group on Novel Breast Ultrasound Technology.

Baker, J A, Kornguth, P., Floyd, C E. Breast imaging reporting and data system standardized mammography lexicon: Observer variability in lesion description. *AJR* 1996; 166:773–778.

Bassett L W, Hendrick R E, Bassford T L, et. al. Quality Determinants of Mammography. AHCPR publication No. 95-0632, Rockville Md., 1994.

Beam C A, Layde P M, Sullivan D C. Variability in the interpretation of screening mammograms by U.S. radiologists. *Archives of Internal Medicine* 1996:156:209–213.

Berg W A, Campassi C, Sexton M J, et al. Analysis of sources of variation in mammographic interpretation. *Radiology* 1997, 205(P): 447.

Bird, R E, Wallace T W, Yankaskas B C. Analysis of cancers missed at screening mammography. *Radiology* 1992, 184:613–617.

D'Orsi, C J, Kopans, D B. Mammographic Feature Analysis. *Seminars in Roentgenology* 1993, 28(3): 204–230.

D'Orsi C J, Bassett L W, Feig S A, Jackson, V P, Kopans, D B, Linver, M N, Sickles E A, Stelling, C B. The American College of Radiology Breast Imaging Reporting and Data System (BI-RADS™). Third Edition. Reston [Va.]: American College of Radiology; 1998.

D'Orsi C J, Bassett L W, Feig S A, Jackson, V P, Kopans, D B, Linver, M N, Sickles E A, Stelling, C B. Illustrated Breast Imaging Reporting and Data System Second Edition. Reston [Va.]: American College of Radiology; 1995.

Elmore J G, Wells C K, Lee C H, Howard D H, Feinstein A R. Variability in radiologists' interpretations of mammograms. *NEJM* 1995; 331:1493–1499.

Elmore J G, Barton M B, Moceri V M, Polk S, Arena P J, Fletcher S W. Ten-year risk of false positive screening mammograms and clinical breast examinations. *NEJM* 1998, 338(16):1089–96.

*Federal Register* 1991, 62: 55988

Hawkins H. et al. Breast Ultrasound Lexicon Illustrated. *Radiology*, 1998; 209(P):523.

Kopans D B, D'Orsi C J, Adler D D, Bassett L W, Brenner R J, Dodd G D, Feig S A, Lopiano M A, McLelland R, Moskowitz M, Sickles E A. The American College of Radiology Breast Imaging Reporting and Data System. American College of Radiology, Reston, Va.: 1993.

Liberman, L, Abramson, A F, Squires, F B, Glassman, J R, Morris, E A, Dershaw, D D. The Breast Imaging Reporting and Data System: Positive predictive Value of mammographic features and final assessment categories. AJR 1998; 171:35–40.

Linver M N, Paster S B, Rosenberg R D, Key C R, Stidley C A, King W V. Improvement in mammography interpretation skills in a community radiology practice after dedicated teaching courses: 2-year medical audit of 38,633 cases. *Radiology* 1992;184:39–43.

Metz C E. ROC methodology in radiologic imaging. *Investigative Radiology* 1986; 21: 720–733.

Orel S G, Sullivan D C, Dambro, T J. BI-RADS categorization as a predictor of malignancy. *Radiology* 1997, 205(P):447

Sickles E A, Ominsky S H, Sollitto R A, Galvin H B, Monticciolo D L. Medical audit of a rapid-throughput mammography screening practice: methodology and results of 27,114 examinations. *Radiology* 1990; 175:323–327.

Shile, P E, Hawkins, H H, O'Neill, M A, Pilgram, T K. Observer Variability in use of Terminology of the American College of Radiology (ACR) Breast Imaging and Reporting Data System (BI-RADS). *Academic Radiology* 1997; 4(12): 850.

Spring, D B, Kimbrell-Wilmot K. Evaluating the success of mammography at the local level: how to conduct an audit of your practice. *Radiologic Clinics of North America* 1987, 25(5); 983–92.

What is claimed is:

1. A method for training radiologists and other interpreters of radiologic studies by tracking their use of feature descriptors and their diagnostic accuracy in the interpretation of radiologic examinations, as well as the health outcome of patients on whom the interpreted examinations are obtained, the method comprising:

tracking each radiologist's characterization of findings in radiologic examinations they interpret using accepted feature descriptors;

tracking each radiologist's assessments and conclusions concerning the presence or absence of biological processes that cause the findings they characterize in radiologic examinations;

tracking evidence for the presence or absence of biologic processes in patients on whom the interpreted examinations have been obtained; and, having each radiologist review tracked data and associated radiologic exams for the purpose of teaching the radiologist to better understand the relationship between feature descriptors and the biologic processes imaged in radiologic examinations, thereby improving the radiologist's diagnostic accuracy and reducing the variability in their use of standardized terminology.

2. The method of claim 1 further including having the radiologist periodically review tracked data and images to determine whether the radiologist's diagnostic accuracy improves and the radiologst's variability in the use of standardized terminology decreases.

3. The method of claim 1 wherein the radiologic examinations are digital radiographic images stored in a computer and viewed on a computer screen or on radiographic film.

4. The method of claim 1 wherein the radiologic examinations are images, or portions of images, viewed on radiographic film or photographic paper.

5. The method of claim 1 wherein the images are from radiologic examinations of a breast.

6. The method of claim 5 wherein the radiologic examinations are interpreted with patient demographic data which can include gender, age, breast cancer risk factors, breast surgical history, or the patient's history of exogenous hormone use.

7. The method of claim 5 wherein the radiologic examinations are imaging examinations of the breast and the radiologist evaluates the images to discriminate between benign and malignant breast disease.

8. The method of claim 7 wherein the images are mammograms.

9. The method of claim 1 wherein the interpreted examinations are a test set of images obtained from groups of patients with defined medical histories or indications for radiologic exams.

10. The method of claim 1 wherein the feature descriptors used by the radiologist are the American College of Radiology's Breast Imaging and Reporting Data System (BI-RADS).

11. The method of claim 1 wherein for the purposes of review, data are collected and tracked for use in Receiver Operator Characteristic (ROC) analysis and presented during exam review as ROC curves and curve areas.

12. The method of claim 1 wherein for the purposes of review, data are collected and tracked to enable calculation of at least one of the following measures of assessing for the presence of a biologic process: positive predictive values, negative predictive values, sensitivity values, specificity values, and likelihood ratios.

13. The method of claim 1 wherein the presence or absence of a biologic process includes the presence or absence of malignant disease and/or the presence or absence of benign disease.

14. The method of claim 1 wherein evidence for the presence or absence of a biologic process includes the histologic results of tissue biopsy.

15. The method of claim 1 wherein evidence for the absence of a biologic process includes no radiologic or clinical evidence of the process.

16. The method of claim 1 wherein tracked data and exams are sorted for presentation to the radiologist during review.

17. The method of claim 16 wherein the tracked data and exams are sorted according to the interpreting radiologist's confidence in, or assessment of, the presence or absence of a biological process.

18. The method of claim 16 wherein the tracked data and exams are sorted according the interpreting radiologist's confidence for or assessment of the presence or absence of malignancy.

19. The method of claim 16 wherein the tracked data and exams are sorted according to the type of biologic process that lead to the radiologic finding.

20. The method of claim 19 wherein the tracked data and exams are further sorted according to the type of histology that lead to the radiologic finding.

21. The method of claim 16 wherein the tracked data and exams are sorted according to the descriptor used to characterize the radiologic finding.

22. The method of claim 1 wherein the tracked data and exams are screening mammography examinations.

23. The method of claim 1 wherein the tracked data and images are from diagnostic mammograms.

24. The method of claim 23 further including tracked data and images from diagnostic mammograms of patients referred for diagnostic evaluation as a result of findings during screening mammograms, using only those examinations where there is a confirmed finding of benign or malignant disease.

25. The method of claim 1 further including tracked data and images from mammographic examinations of patients who are referred for breast biopsy as a result of their mammographic findings.

26. A method for training radiologists and other interpreters of radiologic studies to track and to determine their diagnostic accuracy and use of feature descriptors in the interpretation of radiologic examinations comprising:

preparing a test set of images derived from radiologic examinations of patients;

having the radiologist evaluate defined areas within the images to characterize an abnormality using accepted feature descriptors; and, reviewing the results of the evaluations to determine the radiologist's ability to recognize abnormalities in the images and to properly characterize any abnormalities found using the feature descriptors thereby to improve the radiologist's accuracy of interpretation, reduce the variability in the use of standardized terminology, and train radiologists in understanding the relationship between feature descriptors and pathological entities found in radiologic examinations.

27. A method for training radiologists and other interpreters of radiologic studies that tracks their use of feature descriptors and determines their diagnostic accuracy during interpretation of radiologic examinations and relates these performance data back to the findings in individual radiologic exams, comprising:

preparing a test set of images derived from radiologic examinations of patients;

having the radiologist evaluate defined abnormalites within the images to characterize the abnormalities using accepted feature descriptors and to assess the causes of the abnormalities; and, reviewing their evaluations of the radiologic examinations to determine their ability to accurately assess the causes of abnormalities and to consistently characterize abnormalities using the feature descriptors, thereby training radiologists to understand the relationship between feature descriptors and pathological entities found in radiologic examinations, improving the radiologist's accuracy of interpretation, and reducing variability in the use of standardized terminology.

* * * * *